US011890045B2

(12) United States Patent
Jagadeesan et al.

(10) Patent No.: US 11,890,045 B2
(45) Date of Patent: Feb. 6, 2024

(54) MATERIALS AND TREATMENTS USING PIEZOELECTRIC EMBOLIC MATERIALS

(71) Applicants: Regents of the University of Minnesota, Minneapolis, MN (US); MicroVention, Inc., Aliso Viejo, CA (US)

(72) Inventors: Bharathi Jagadeesan, North Oaks, MN (US); Sean Lester Moen, Saint Paul, MN (US); George R. Greene, Jr., Costa Mesa, CA (US)

(73) Assignees: Regents of the University of Minnesota, Minneapolis, MN (US); MicroVention Inc., Aliso Viejo, CA (US)

( * ) Notice: Subject to any disclaimer, the term of this patent is extended or adjusted under 35 U.S.C. 154(b) by 271 days.

(21) Appl. No.: 15/912,187

(22) Filed: Mar. 5, 2018

(65) Prior Publication Data

US 2018/0250058 A1    Sep. 6, 2018

Related U.S. Application Data

(60) Provisional application No. 62/466,496, filed on Mar. 3, 2017.

(51) Int. Cl.
*A61B 18/06* (2006.01)
*A61L 24/00* (2006.01)
(Continued)

(52) U.S. Cl.
CPC ........ *A61B 18/06* (2013.01); *A61B 17/12186* (2013.01); *A61B 18/04* (2013.01);
(Continued)

(58) Field of Classification Search
CPC ......... A61B 18/06; A61B 18/04; A61B 18/18; A61B 17/12186; A61B 2090/3966;
(Continued)

(56) References Cited

U.S. PATENT DOCUMENTS

2002/0087151 A1    7/2002   Mody
2004/0199156 A1   10/2004   Rioux
(Continued)

FOREIGN PATENT DOCUMENTS

CN    102895197    1/2013
CN    103550832    2/2014
(Continued)

OTHER PUBLICATIONS

Il'ina MV, Il'in OI, Blinov YF, Konshin AA, Konoplev BG, Ageev OA. Piezoelectric Response of Multi-Walled Carbon Nanotubes. Materials (Basel). Apr. 21, 2018;11(4):638. (Year: 2018).*
(Continued)

*Primary Examiner* — Theodore J Stigell
*Assistant Examiner* — Rachel T. Smith
(74) *Attorney, Agent, or Firm* — Merchant & Gould P.C

(57) ABSTRACT

An embolic agent and a piezoelectric substance are mixed together. The mixture can be delivered to a tumor or other object by a non-invasive method. The embolic agent prevents movement of the piezoelectric substance from the target location. Subsequent impulses applied to the target location cause ablation of the surrounding area due to the piezoelectric effect of the particles, promoting highly accurate and precise ablation without the need for more invasive procedures.

7 Claims, 1 Drawing Sheet

(51) Int. Cl.
*A61L 24/02* (2006.01)
*A61B 17/12* (2006.01)
*A61L 24/06* (2006.01)
*A61N 7/02* (2006.01)
*A61B 18/04* (2006.01)
*A61N 5/00* (2006.01)
*A61B 18/18* (2006.01)
*A61B 18/00* (2006.01)
*A61M 37/00* (2006.01)
*A61B 90/00* (2016.01)

(52) U.S. Cl.
CPC ............. *A61B 18/18* (2013.01); *A61L 24/00* (2013.01); *A61L 24/001* (2013.01); *A61L 24/02* (2013.01); *A61L 24/06* (2013.01); *A61N 5/00* (2013.01); *A61N 7/02* (2013.01); *A61B 2018/00577* (2013.01); *A61B 2090/3966* (2016.02); *A61L 2400/06* (2013.01); *A61L 2430/36* (2013.01); *A61M 37/0092* (2013.01)

(58) Field of Classification Search
CPC .... A61B 2018/00577; A61B 17/12181; A61B 2017/22082; A61B 2017/22085; A61B 2017/22088; A61L 24/001; A61L 24/00; A61L 24/02; A61L 24/06; A61L 2400/06; A61L 2430/36; A61N 7/02; A61N 5/00; A61N 2007/0043; A61N 2007/0047; A61M 37/0092; A61M 2205/058; A61K 41/0028; A61K 41/0033; A61K 49/222; A61K 9/5094; A61K 9/0009; A61K 49/0452; A61K 51/1244; A61P 43/00

See application file for complete search history.

(56) References Cited

U.S. PATENT DOCUMENTS

| | | | |
|---|---|---|---|
| 2008/0026069 A1* | 1/2008 | Lanphere | A61P 35/00 428/402 |
| 2009/0054535 A1* | 2/2009 | Figuly | A61L 24/043 514/777 |
| 2009/0169471 A1 | 7/2009 | Richard et al. | |
| 2010/0184669 A1 | 7/2010 | Harrison | |
| 2011/0118533 A1* | 5/2011 | Hawkett | A61K 9/0019 600/9 |
| 2011/0196347 A1 | 8/2011 | Atansoska | |
| 2011/0280947 A1* | 11/2011 | Rioux | A61P 43/00 424/499 |
| 2014/0228840 A1* | 8/2014 | Berry | A61P 35/00 606/41 |
| 2015/0265725 A1* | 9/2015 | Peyman | A61K 45/06 600/2 |
| 2016/0287258 A1* | 10/2016 | Connolly | A61B 17/1219 |

FOREIGN PATENT DOCUMENTS

| | | |
|---|---|---|
| CN | 103550834 | 2/2014 |
| CN | 104066450 | 9/2014 |
| CN | 105462142 | 4/2016 |
| WO | WO 2013/049600 | 4/2013 |
| WO | WO2015123082 A1 | 8/2015 |
| WO | WO2015195625 A1 | 12/2015 |
| WO | WO2018/161080 | 9/2018 |

OTHER PUBLICATIONS

International Search Report and Written Opinion, Application No. PCT/US18/20931, filed May 15, 2018, 18 pages.

Ghosh et al., "Increased Heating Efficiency and Selective Thermal Ablation of Malignant Tissue with DNA-Encased Multiwalled Carbon Nanotubes," ACS Nano (oneline), 2009, vol. 3, No. 9, pp. 2667-2673.

Chinese Office Action, Application No. 201880024992.8, dated May 21, 2020, 5 pages.

Chinese Search Report, Application No. 201880024992.8, dated May 13, 2020, 3 pages.

Christopher J. Gannon et al., "Carbon nanotube-enhanced thermal destruction of cancer cells in a noninvasive radiofrequency field", Cancer, vol. 110, No. 12, Dec. 15, 2007, pp. 2654-2665, XP055722940, US ISSN: 0008-543X, DOI: 10.1002/cncr.23155.

European Search Report, European Application No. 18761963.0, dated Nov. 10, 2020, 9 pages.

Chinese Office Action, Chinese Application No. 201880024992.8, dated Nov. 19, 2020, 6 pages.

"Antiferromagnetism," Encyclopaedia Britannica, Inc., https://www.britannica.com/science/antiferromagnetism, accessed Jan. 26, 2021.

European Search Report, European Application No. 18761963.0, dated Feb. 11, 2021, 7 pages.

* cited by examiner

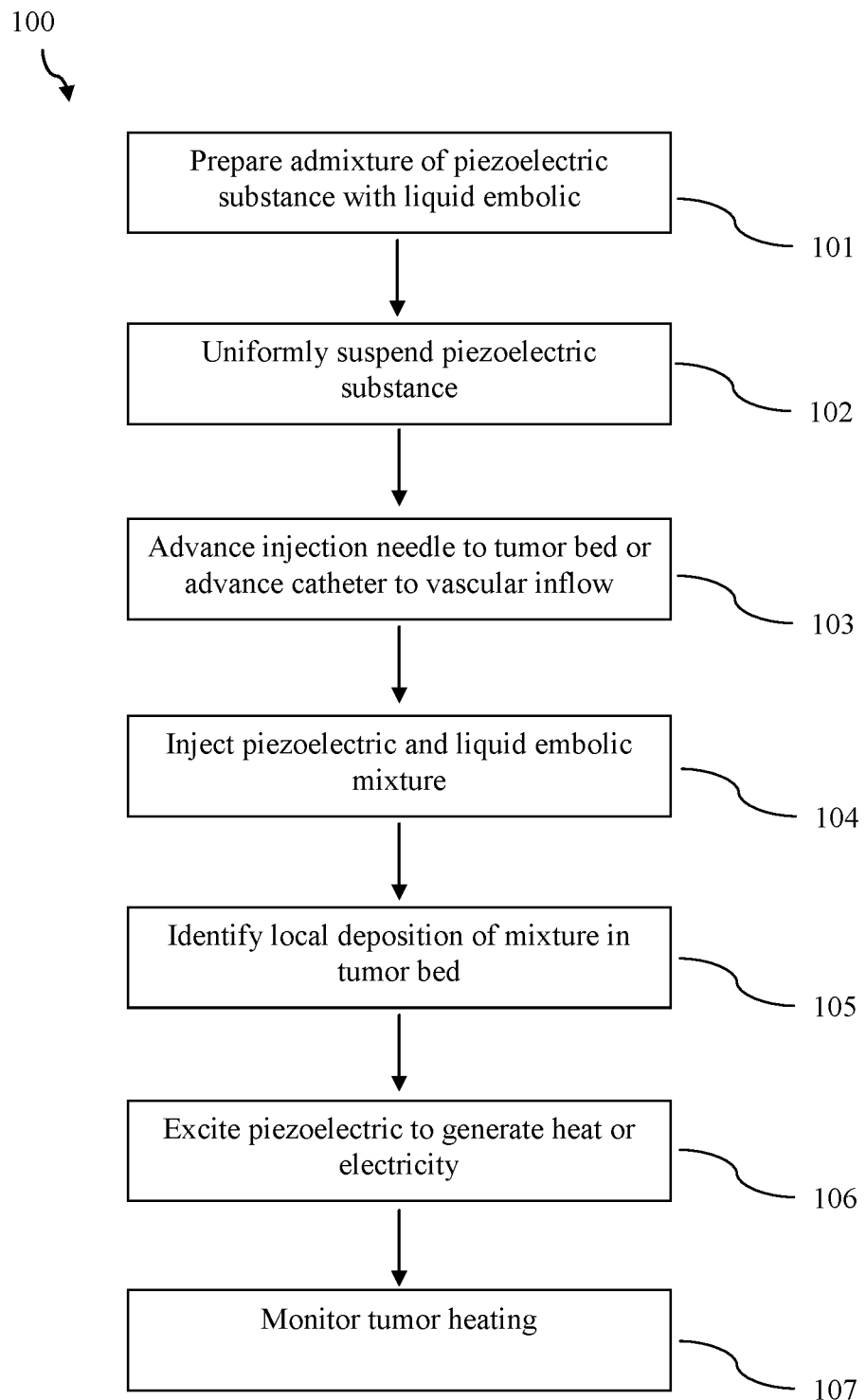

:

MATERIALS AND TREATMENTS USING PIEZOELECTRIC EMBOLIC MATERIALS

RELATED APPLICATION

The present application claims the benefit of U.S. Provisional Application No. 62/466,496 filed Mar. 3, 2017, which is incorporated herein by reference in its entirety.

TECHNICAL FIELD

Embodiments relate to surgical instruments, devices or methods for transferring non-mechanical forms of energy to or from the body, in particular ablation for precise removal of tumors.

BACKGROUND

Tumors can be treated using a variety of conventional techniques. Tumors can be reduced or eliminated by ablation, while other techniques remove the blood supply to the tumor, such as by embolization or injection of particles having radioisotope beads.

Some of these technologies for treating tumors use embolic materials to create tumor necrosis, irradiate the tumor cells with external or implanted sources of radiation, or perform high intensity focused ultrasound with or without magnetic resonance imaging (MRI) guidance to produce thermal ablation of tumors. In some experimental techniques, it has been attempted to localize piezoelectric substances where the tumor is located. Typically these attempts have relied on intravenously injecting targeted piezo-electrical substances that are then taken up by tumor cells. The theoretical basis of such experimental attempts rests in the fact that successful deposition of piezo-electric compounds to tumors can enhance the effectiveness of HIFU treatment by augmenting destructive energy delivered to the tumor. Piezoelectric substances or particles respond to mechanical stimulus, such as the acoustic energy of the ultrasound waves, by producing a corresponding electrical current, and radiofrequency ablation can then be achieved locally, which augments the destructive power of high intensity focused ultrasound (HIFU). Conversely, once piezo-electric substances are deposited in tissue, their exposure to RF pulses from MRI machines can result in generation of ablative acoustic/mechanical energy by these crystals. Hence by achieving reliable focal deposition of these crystals in tumors, HIFU procedures (with or without MRI guidance) as well as ablative MRI procedures can be made more effective and tumor ablation can be achieved at lower energies or greater depths.

Previous attempts at using piezo-electric substances for ultrasound or MR ablation have relied on intravenous injection of these agents, and suffer from poor tumor concentration of these agents and high background uptake. Therefore, intravenous injection of piezoelectric substances before ablation and subsequently using ultrasound can result in damage to surrounding tissue. Furthermore, delivering the piezoelectric substance to the appropriate depth and in an adequate dosage is challenging. Therefore, while piezoelectric substances aid in ablation, they are difficult to accurately and precisely deliver, in order to ensure that the entire tumor is ablated, and furthermore to limit damage to surrounding tissues.

SUMMARY

According to embodiments, a tumor treatment compound includes a liquid embolic material coupled with piezoelectric materials.

A method for using the compound produces a high local concentration of the piezoelectric agent, which can be delivered in combination with the liquid embolic into a tumor either via direct needle injection or intra-vascular injection, in embodiments. High-intensity focused ultrasound, with or without magnetic resonance (MR) guidance, can then be delivered to the treatment site from an extracorporeal ultrasound transducer, which will ablate the tumor with high levels of precision. Alternatively, radio frequency (RF) pulses can be used with a magnetic resonance imaging (MRI) machine to produce MR ablation.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 1 is a flowchart of a method for delivering a mixture used for ablation according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Ablation of a tumor can take place through delivery of electrical current or charge, heating, exposure to ionizing radiation or mechanical energy. Conventional techniques use these, as well as direct resection or chemical treatments, to remove or destroy tumors. It is desirable to reduce the amount of unnecessary damage to adjacent tissues during destruction of the tumor while adequately destroying tumor cells to prevent recurrence.

In some cases, it may be possible to perform a surgical operation to directly resect the tumor or growth. In other circumstances, however, surgery may be dangerous to the health of the patient. Even where surgery would not be particularly dangerous, it may nevertheless be preferable to treat a tumor using a minimally invasive or non-invasive treatment. Two such non-invasive mechanisms for destroying a tumor include cutting off blood flow to the tumor and ablating the tumor.

One method for treatment of a tumor or other growth is to reduce or eliminate the blood flow to a tumor using embolic agents. For example, particulate or liquid embolic agents can be delivered to an artery that is providing a blood supply to a tumor. Without the resources from the blood flow, the tumor cannot survive and will deteriorate. An embolic agent can also be directly injected into the tumor (by percutaneous or direct intra-operative visualization, for example).

Ablation can be accomplished in several ways. For example, radio-frequency electrical ablation can be delivered to a tumor. Energy to ablate a tumor can be delivered by other mechanisms as well, such as by ultrasound. Some treatments employ radiation from an injected substance, such as microbeads of yttrium 90 that are injected at the site of the tumor. Use of these non-surgical mechanisms should nonetheless be targeted as precisely as possible.

It can be difficult to deliver radio frequency or ultrasound energy precisely to a tumor when the tumor is deep in the body or adjacent to a major blood vessel. Embolic agents can however often be delivered quite precisely, using catheters or needles to deliver the embolic to a specific location. The catheter or needle can be guided using fluoroscopy or ultrasound, for example, to target the embolic material to a very specific location. Furthermore, once the embolic material, in particular liquid embolic material, is delivered to the location, it solidifies and remains securely in place without systemic disbursement as the vascular supply to the area has been occluded.

According to an embodiment, a mixture of embolic and piezoelectric materials is delivered to the site of a tumor or other object for ablation. The mixture can be precisely delivered, because the embolic prevents significant movement of the mixture after delivery by reducing or eliminating blood flow in the direct vicinity of the injected material. An injectable liquid embolic agent mixed with piezoelectric material, in conjunction with high intensity focused ultrasound (HIFU) or magnetic resonance imaging (MRI), can be used for tumor ablation. The mixture can be delivered to a tumor in a minimally invasive manner, and the liquid embolic agent enables specific localization and retention of the piezoelectric material in the tumor tissue while also reducing blood flow to the tumor. Subsequently, when HIFU beams are delivered to the tumor, the piezoelectric material deposited in the tumor produces an increase in treatment zone temperature. This effect can potentially result in tumor ablation with relatively low HIFU energies. In addition, the embolic agent and piezoelectric crystals can serve as an echogenic target for the HIFU transducer and are therefore easily targetable. Such easy visualization of the target lesion can also help with treatment planning and HIFU beam modeling in conjunction with techniques such as time reversal which are frequently used when HIFU is targeted at deep tissues.

After the material is delivered to a target location, the piezoelectric component of the material can be activated by delivery of an electrical or mechanical impulse. Ultrasound delivered to a mixture of embolic and piezoelectric material can generate electrical impulses that will ablate tissue in the vicinity. Likewise, electromagnetic energy (such as radio frequency waves) will cause mechanical deformation of the piezoelectric material. By tuning the frequency and amplitude of the impulse delivered to the piezoelectric material, a desired electrical or mechanical output can be produced at the location of the object.

In embodiments, the piezoelectric material can include carbon nanotubes, titanium dioxide, or other biocompatible piezoelectric substances. In some embodiments, the piezoelectric material can include pulverent material, nanoparticles, powders, granules, or other substances that can be dispersed throughout the embolic material. The piezoelectric material translates electrical energy input into mechanical energy output and/or vice versa.

Likewise, the embolic material can be any of a variety of biocompatible embolic materials, including liquid embolic materials. The embolic material can further be chosen such that the piezoelectric material does not cause precipitation thereof, or alternatively the piezo-electric material can be chosen to not cause precipitation of the embolic material. In some embodiments, the embolic material can be ethylene vinyl alcohol or another biocompatible copolymer dissolved in dimethyl sulfoxide (DMSO). For example, the embolic agent could be one of the commercially available products sold under the ONYX®, TRUFILL®, or PHIL® lines. All these embolic agents solidify based on exposure to materials of a certain pH, so when these agents contact blood they solidify or harden in response to reacting to the pH of blood. In other embodiments, the embolic material can be an adhesive. The piezoelectric material can be delivered along with the embolic material, where the embolic material acts as a carrier for the piezoelectric while further keeping the piezoelectric from migrating as the embolic hardens or solidifies in the bloodstream.

ONYX® utilizes an ethylene vinyl alcohol biocompatible copolymer dissolved in DMSO and radiopaque tantalum particles or powder used for visualization and is described in more detail in U.S. Pat. No. 5,851,508 which is hereby incorporated by reference in its entirety. TRUFILL® utilizes an n-butyl cyanoacrylate biocompatible copolymer. PHIL® is made of a HEMA (hydroxyethyl methacrylate) and triiodophenol (lactide co-glycolide) acrylate and is comprised of a biocompatible polymer suspended in a DMSO solution, where iodine is bonded directly to the polymer backbone to aid in visualization. PHIL® is soluble in DMSO but insoluble in an aqueous environment. Upon contact with blood, PHIL® begins to precipitate. The DMSO diffuses through the tissue and a resultant solid polymer remains in the target vessel. PHIL® is further described in U.S. Pat. No. 9,078,950 which is hereby incorporated by reference in its entirety. PHIL® is sold as a prepackaged syringe comprised of the homogenous radiopaque polymer in solution with the organic solvent DMSO. Other liquid embolic can utilize an aqueous solution, such as the embolic described in U.S. Pat. No. 9,351,993 which is hereby incorporated by reference in its entirety. The particular embolic material described therein utilizes a polymer comprising various acrylates (tetrabutylacrylate and hydroxybutylacrylate) dissolved in an aqueous solution, and radiopaque barium sulfate particles used for visualization. The polymer is dissolved in the aqueous solution in the delivery syringe and then reacts to the pH of blood to harden or solidify in the vasculature.

In one embodiment, the piezo-electric material is mixed with the embolic material. For instance, the piezo-electric material can be added as a component to the pre-filled PHIL® syringe, so that the piezoelectric material is delivered with the embolic material. To prevent separation of the piezoelectric material from the embolic material, the syringe can be shaken or agitated (e.g., by hand, or with a centrifuge) prior to embolic material delivery to ensure the piezoelectric material is evenly dispersed with the embolic material. Piezo-electric materials lacking aqueous content can be used to prevent premature precipitation or solidification of the embolic polymer, in embodiments in which contact with water would cause the embolic material to solidify. Since many liquid embolics are mixed or delivered with DMSO to prevent early solidification, the piezoelectric material can be made of material that will not degrade in response to DMSO exposure. Since water is a significant component of blood, piezoelectric material that is insoluble in water is preferable to prevent the piezoelectric material from dissolving in blood. Many piezoelectric materials can potentially meet these requirements including, for example, polyvinylidene fluoride, barium titanate, and bismuth titanate. The individual piezo-electric crystals/particles/components, in one example, are sized to be about 500 micrometers or less, about 0.5 micrometers to about 5 micrometers, or about 2 micrometers on average.

In one embodiment, the piezo-electrical material is chemically bound to the biocompatible embolic polymer. This could negate the need to agitate the delivery syringe to ensure proper mixing of the piezo-electric material prior to delivery since the piezo-electrical material would be part of the polymer structure itself.

FIG. 1 is a flowchart of a method 100 according to an embodiment in which a piezoelectric and embolic mixture is delivered to a tumor.

At 101, an admixture of a piezoelectric substance and a liquid embolic is prepared. The mixture could be, for example, up to 10% piezoelectric mixed with greater than 90% liquid embolic material. Depending on the type of liquid embolic used, the liquid embolic material could either include solely the biocompatible polymer, or in some embodiments could include a biocompatible polymer along with a solvent such as DMSO or an aqueous solution such that the biocompatible polymer can be dissolved or suspended therein. In alternative embodiments, the mixture could be up to 5%, up to 20%, or up to 30% piezoelectric, with liquid embolic making up the rest of the mixture. In other embodiments, additional materials could be added to the mixture, such as coagulants, solvents, or other materials to promote uniform distribution of the piezoelectric particles and ensure embolization occurs as desired.

At 102, the piezoelectric is suspended in the mixture uniformly. By suspending the piezoelectric substance uniformly, the mixture can be used to produce a known quantity of charge or motion when activated by mechanical or electrical impulse. Various techniques can be used to achieve this uniform suspension. In some examples, mechanical agitation (e.g., shaking) can be used to create this uniform suspension. In some examples, the user would transfer the contents between a pre-provided embolic syringe and an empty syringe, back and forth, in order to create a uniform suspension. In other examples, a centrifuge or vortex agitator is used. In one example, once the step is taken to uniformly suspend the piezoelectric in the mixture, a needle is used to draw the mixture of the embolic material and suspended piezoelectric into a separate syringe; the contents of this separate syringe are then injected into the patient.

In one particular example, a pre-filled syringe sold to the end user would include PHIL® in the form of the biocompatible polymer suspended in DMSO and separate piezoelectric particles/material all included in said pre-filled syringe. The user would use a vortex agitator to agitate the syringe so that the piezoelectric material is suspended in the syringe, and the contents of this syringe would then be transferred to another delivery syringe via a needle. This delivery syringe could then be used to deliver the mixture into the patient's bloodstream.

At 103, a delivery device such as a needle or catheter configured to deliver the mixture is advanced to the tumor bed. In one embodiment, a needle is advanced to the tumor bed, and alternatively a catheter can be routed through the vasculature to a vein or artery at a vascular inflow to a tumor.

At 104, the piezoelectric and liquid embolic mixture is delivered to the tumor or tumor bed by the needle or catheter from 103. In embodiments, the mixture can be delivered to a region or multiple insertion points, rather than a single location. In embodiments, fluoroscopy or ultrasound can be used to determine the precise position of the needle during advancement or injection at 103 and 104. The mixture is injected to areas which are to be ablated, such as a tumor. During and after injection, the local deposition of the mixture in the tumor bed can be identified, at 105. In embodiments, the piezoelectric material that has been injected can be used to identify the local depositions, based on feedback produced by the piezoelectric particles in response to electrical or mechanical stimuli.

An advantage of the mixture of the liquid embolic and piezoelectric materials is the ability to better place the piezoelectric materials and keep them from migrating. With conventional radioactive bead delivery, the radioactive beads are simply carried by the arterial flow to the capillaries where they embolize the vessel and deliver localized radiation to the targeted tumor. By using a liquid embolic combined with the piezoelectric materials, the piezoelectric materials can be placed closer to the targeted region and in locations that are not in the vasculature, such as by direct injection into a tumor. Placement of piezoelectric materials close to the targeted site is important to minimize damage to the surrounding healthy tissue. The use of piezoelectric materials also avoids the need to deal with the limited half-lives, transportation, and handling of radioactive material such as radioactive beads, and costs associated with those radioactive materials.

At 106, the piezoelectric material is excited to generate heat (by application of electrical impulse such as RF impulse) or electricity (by application of mechanical impulse such as ultrasound). Because the mixture including an embolic is injected at the tumor bed or other areas which are desirably ablated, there is little or no spread of the piezoelectric to other areas. In this way, an ultrasonic impulse can be delivered that is not sufficient to damage tissue, but will cause generation of electricity and corresponding ablation only in the region where the piezoelectric and embolic mixture has been delivered. Likewise, an electromagnetic impulse such as an RF impulse could be delivered that is not sufficient to cause damage to tissue alone, but which causes mechanical deformations in the piezoelectric that ablates tissue by heating.

In embodiments, the piezoelectric material can be chosen such that it effectively acts as a receiver. Ultrasound and RF impulses pass through a patient, dissipating as a function of distance traveled. When those impulses reach a piezoelectric particle, however, they are absorbed more rapidly than they would be by surrounding tissues. The energy absorbed by the piezoelectric is dissipated, either electrically (for incoming mechanical impulses like ultrasound) or mechanically (for incoming electromagnetic impulses like RF waves).

At 107, tumor heating is monitored. When sufficient heating occurs at the site of the tumor or other object, a medical professional can determine that the object has been ablated.

In embodiments, a kit or system can be provided for use by a medical practitioner to ablate a tumor. Such a kit could include all of the components sufficient to ablate a tumor or other object as described above. For example, a kit could include a delivery needle, a quantity of an embolic agent, and a quantity of a piezoelectric material. In one embodiment, the kit includes a delivery needle, a pre-packaged syringe including embolic material (e.g., either a biocompatible polymer, or the biocompatible polymer suspended or dissolved in a solvent such as DMSO or an aqueous solution), and additional syringes (which can in turn contain DMSO, aqueous solution, saline, or other solvents). In another embodiment, an empty syringe for placement of the final deliverable embolic mixture is further included. In some embodiments, the kit could further include an apparatus for mixing or emulsing the embolic and piezoelectric materials—such as a vortex agitator, or a separate syringe for mixing the materials back and forth to uniformly suspend the piezoelectric materials.

The mixing apparatus could be a mixing tip or cartridge, vortex agitator or centrifuge, or it could be a jar or other container with a stir rod, in embodiments. For example, mixing tips are known which are conventionally used to combine the parts of a 2-part epoxy. Such mixing tips could be configured to combine the embolic agent and the piezoelectric material prior to delivery to the object by the delivery apparatus. In embodiments, mixing can occur in the delivery apparatus itself. For example, the delivery apparatus could be a delivery needle having multiple internal channels which are configured for mixing.

Alternatively, rather than a delivery needle, the kit could include a catheter for delivery of the mixture to a part of the vascular system of a patient. Microcatheters can be used to deliver the embolic material and piezoelectric material to a desired target. In embodiments, a catheter should be configured to mix an embolic agent and a piezoelectric material as well. For example, one internal microcatheter could provide a source of embolic agent, whereas another internal microcatheter could provide a source of piezoelectric material suspended in a solvent or other carrier material, and the two sources could be mixed internally prior to delivery at the distal end of the catheter.

In embodiments, a kit could include a predetermined quantity of each of the embolic agent and the piezoelectric material in a predefined ratio, such at 10% piezoelectric material : 90% embolic agent by weight. As described above in more detail, depending on which type of embolic material is used the embolic material could be a solidifying biocompatible polymer, or the embolic material could include both the biocompatible polymer and a solvent (e.g., aqueous solution or DMSO) that holds the biocompatible polymer.

Various other components may be useful in embodiments, such as basic supplies needed for an operation such as sutures, disinfectant wipes, or materials and supplies to assist in delivery of mechanical or electromagnetic signal to activate the piezoelectric material, or materials and supplies to assist in guiding the mixture of embolic and piezoelectric materials to the proper location using fluoroscopy, MRI, or other procedures. Such kits or systems can be packaged and provided to medical professionals for use in ablation of tumors or other objects.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A system for ablation of a tumor bed, the system comprising:
 a first predetermined quantity of an embolic agent;
 a second predetermined quantity of a biocompatible piezoelectric material comprising titanium dioxide, wherein the biocompatible piezoelectric material is chosen such that the second predetermined quantity of the biocompatible piezoelectric material does not cause precipitation of the embolic agent; and
 a delivery apparatus configured to provide a mixture of the embolic agent and the piezoelectric material directly to the tumor bed such that the embolic agent keeps the piezoelectric material from migrating and the embolic agent solidifies and remains securely in place, wherein the delivery apparatus is a needle configured to be directly inserted into the tumor bed.

2. The system of claim 1, further comprising a mixing apparatus.

3. The system of claim 2, wherein the mixing apparatus is a mixing tip configured to combine the embolic agent and the biocompatible piezoelectric material.

4. The system of claim 2, wherein the mixing apparatus is a vortex agitator.

5. The system of claim 2, wherein the mixing apparatus is a separate syringe.

6. The system of claim 1, wherein the delivery apparatus is configured to mix the embolic agent and the biocompatible piezoelectric material.

7. The system of claim 1, wherein the first predetermined quantity is greater than or equal to 90% of a total weight of the mixture of the embolic agent and the biocompatible piezoelectric material and the second predetermined quantity is less than or equal to 10% of the total weight of the mixture of the embolic agent and the biocompatible piezoelectric material.

* * * * *